(12) United States Patent
Dininno et al.

(10) Patent No.: US 6,310,055 B2
(45) Date of Patent: *Oct. 30, 2001

(54) HALOPHENOXY SUBSTITUTED CARBAPENEM ANTIBACTERIAL COMPOUNDS

(75) Inventors: Frank P. Dininno, Old Bridge; Kevin D. Dykstra, West Milford, both of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/311,519

(22) Filed: May 13, 1999

Related U.S. Application Data

(60) Provisional application No. 60/087,722, filed on Jun. 2, 1998.

(51) Int. Cl.[7] .................. A61K 31/407; A61K 31/4995; C07D 477/12; C07D 519/06; A61P 31/04
(52) U.S. Cl. ........................ 514/210.09; 540/302
(58) Field of Search ................. 514/210.09; 540/302

(56) References Cited

U.S. PATENT DOCUMENTS

| 4,309,438 | 1/1982 | Christensen et al. | 540/350 |
| 4,479,947 | 10/1984 | Christensen | 540/350 |

FOREIGN PATENT DOCUMENTS

| 0 007 614 | 2/1980 | (EP) . |
| 0 072 014 | 2/1983 | (EP) . |

OTHER PUBLICATIONS

Kevin D. Dykstra & Frank Dininno, Tet. Ltrs. 39: 1865–1868 (1998).
Michael E. Jung & Lynn A. Light, Tet. Ltrs. 23(38): 3851–3854 (1982).
W. M. Stanley et al., JACS, 55: 706–716 (1933).

*Primary Examiner*—Mark L. Berch
(74) *Attorney, Agent, or Firm*—Sylvia A. Ayler; Mark R. Daniel

(57) ABSTRACT

The present invention relates to carbapenem antibacterial agents in which the carbapenem nucleus is substituted at the 2-position with a iodophenoxy linked through a group —Z—CH$_2$—; The compound is further substituted with various substituent groups including at least one cationic group.

The compounds are represented by formula I:

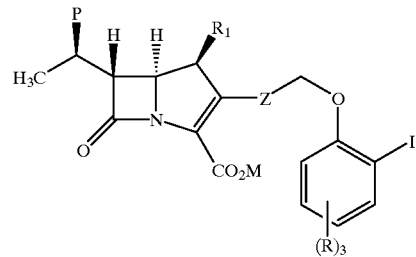

wherein Z represents trans-ethenediyl or ethynediyl.

Pharmaceutical compositions and methods of use are also included.

24 Claims, No Drawings

HALOPHENOXY SUBSTITUTED CARBAPENEM ANTIBACTERIAL COMPOUNDS

This application claims the benefit of U.S. Provisional Application No. 60/087,722, filed Jun. 2, 1998.

BACKGROUND OF THE INVENTION

The present invention relates to carbapenem antibacterial agents in which the carbapenem nucleus is substituted at the 2-position with a iodophenoxy linked through a group —Z—$CH_2$—. Z represents an trans-ethenediyl or ethynediyl group. The iodophenoxy is further substituted with various substituent groups including at least one cationic group.

The carbapenems of the present invention are useful against gram positive microorganisms, especially methicillin resistant Staphylococcus aureus (MRSA), methicillin resistant *Staphylococcus epidermidis* (MRSE), and methicillin resistant coagulase negative Staphylococci (MRCNS). The antibacterial compounds of the present invention thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The present invention relates to anti-MRSA carbapenem antibiotics containing aromatic based side-chains linked via an alkoxy unsaturated group. The side-chain imparts MRS activity previously unassociated with the carbapenem skeleton.

The compounds of the invention are represented by formula I:

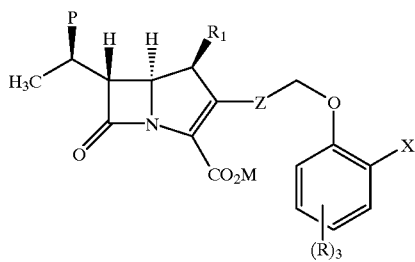

or a pharmaceutically acceptable salt thereof, wherein:

$R^1$ represents H or methyl;

$CO_2M$ represents a carboxylic acid, a carboxylate anion, a pharmaceutically acceptable ester group or a carboxylic acid protected by a protecting group;

X represents a halogen such as iodine, bromine, chlorine or fluorine;

P represents hydrogen, hydroxyl, F or hydroxyl protected by a hydroxyl-protecting group;

Z represents trans-ethenediyl or ethynediyl;

each R is independently selected from: —R*; —Q; hydrogen; halo; —CN; —$NO_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; —OC(O)$R^a$; —OC(O)$NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups and A—$(CH_2)_n$—Q, wherein A is O, S, or $CH_2$, and n is 0–3;

each $R^a$, $R^b$ and $R^c$ independently represents hydrogen, —R*, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —C($NR^e$)$NR^fR^g$; —$NR^eC(NH)NR^fR^g$; —$NR^eC(NR^f)R^g$; —R* or —Q;

$R^e$, $R^f$ and $R^g$ represent hydrogen; —R*; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —N($R^h$)$_2$; —$N^+$(Rh)$_3$; —C(O)N($R^h$)$_2$; —$SO_2$N($R^h$)$_2$; heteroaryl; heteroarylium; —$CO_2R^h$; —C(O)$R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

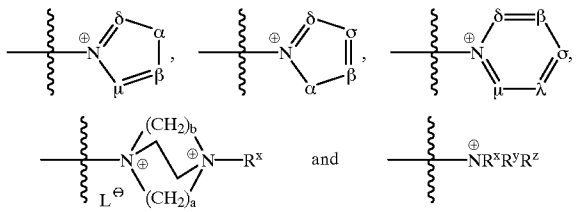

wherein:

a and b are 1, 2 or 3;

$L^-$ is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

R* is selected from the group consisting of:

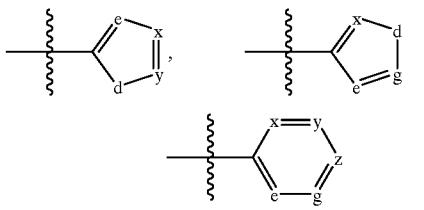

and wherein:
d represents O, S or $NR^k$;

e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR''R^o$; —$OR''$; —$SR''$; —$CONR''R^o$; —$COOR^h$; —$SOR''$; —$SO_2R''$; —$SO_2NR''R^o$; —$NR''SO_2R^o$; —$COR''$; —$NR''COR^o$; —$OCOR''$; —$OCONR''R^o$; —$NR''CO_2R^h$; —$NR''CONR^oR^h$; —$OCO_2R^h$; —$CNR''NR^oR^h$; —$NR''CNHNR^oR^h$; —$NR''C(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR''R^v$; —$OR''$; —$SR''$; —$CONR''R^v$; —$COOR^h$; —$SOR''$; —$SO_2R''$; $SO_2NR''R^v$; —$NR''SO_2R^v$; —$COR''$; —$NR''COR^v$; —$OCOR''$; —$OCONR''R^v$; —$NR''CO_2R^v$; —$NR''CONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^W$ or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, NRW, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups.

Pharmaceutical compositions and methods of treatment are also included herein.

DETAILED DESCRIPTION OF THE INVENTION

The invention is described herein in detail using the terms defined below unless otherwise specified.

Carboxylate anion refers to a negatively charged group —COO⁻.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical, straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical, straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

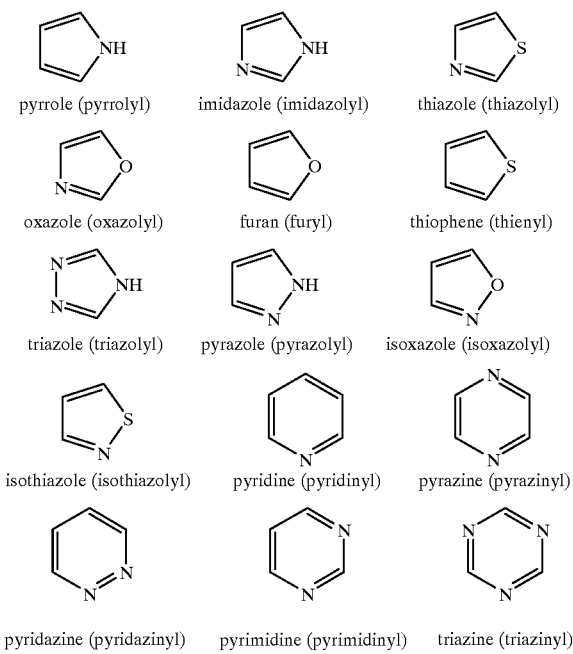

Heteroarylium refers to heteroaryl groups bearing a quaternary nitrogen atom and thus a positive charge. Examples include the following:

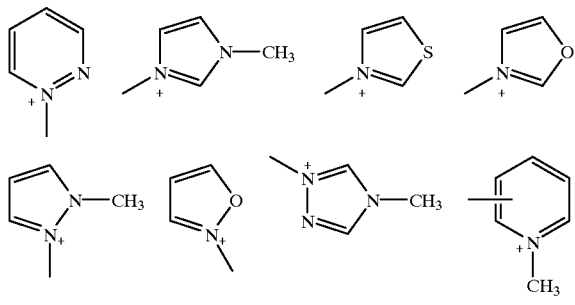

-continued

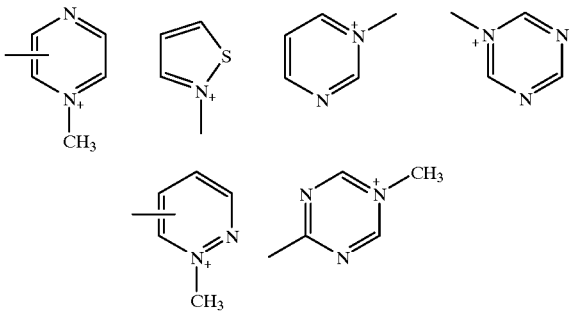

When a charge is shown on a particular nitrogen atom in a ring which contains one or more additional nitrogen atoms, it is understood that the charge may reside on a different nitrogen atom in the ring by virtue of charge resonance that occurs.

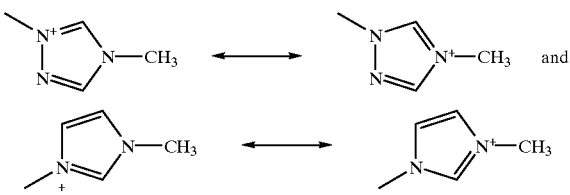

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, N.Y. (1991). Examples of suitable protecting groups are contained throughout the specification.

When an alkyl group is "interrupted by" 1 or more moieties, such as O, S, N, —C(O)— and the like, this includes alkyl groups which are terminated by the moiety or moieties, as well as alkyl groups that are interrupted or terminated by combinations of such groups. Thus for example, —C(O)O—, —OC(O)—, —C(O)NR$^8$— and similar such moieties are included. Examples of alkyl groups terminated by the moiety or moieties are as follows: —O—C$_{1-6}$ alkyl, —C$_{1-6}$ alkyl-O—, —C$_{1-6}$ alkyl-OC(O)—, —O—C$_{1-6}$ alkyl-S— and the like. Obviously other moieties are included in accordance with the general description contained herein.

In some of the carbapenem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBS), phenacyl, p-methoxybenzyl, o-nitrobenzyl, p-methoxyphenyl, p-nitrobenzyl, 4-pyridylmethyl and t-butyl.

Examples of suitable hydroxyl protecting groups include triethylsilyl (TES), t-butyldimethylsilyl (TBS), t-butyldiphenylsilyl (DPTBS), o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —CO$_2$M, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

L$^-$ can be present or absent as necessary to maintain the appropriate charge balance. When present, L$^-$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L– represents a specie with more than one negative charge, such as malonate, tartrate or ethylenediamine-tetraacetate (EDTA), an appropriate number of carbapenem molecules can be found in association therewith to maintain the overall charge balance and neutrality.

At least one of the R groups attached to the phenoxy platform can optionally contain a positively charged moiety. Thus, it can include —R* or Q, or a moiety which in turn contains a positively charged group.

A subset of compounds of formula I which is of interest relates to those compounds where $CO_2M$ represents a carboxylate anion. Hence, M in this instance represents a negative charge which will be balanced by a positively charged group, such as in the positively charged R group. Likewise, if the positively charged R group contains more than one positive charge, a negatively charged counterion may be present which in combination with the carboxylate anion, provides overall charge neutrality.

Another subset of compounds of formula I which is of interest relates to compounds wherein one R represents a group which contains a positively charged moiety, and the remaining R groups are selected from hydrogen and $C_{1-6}$ straight or branched chain alkyl, unsubstituted or substituted with one to four $R^d$ groups. More particularly, this subset of interest includes compounds of formula Ia wherein one R represents a group containing a positively charged moiety and the remaining R groups are hydrogen.

With respect to the positively charged moiety or moieties that are contained in one or more R groups, it is preferred that from 1–3 positive charges be present, and most preferably one positive charge be present, balanced by the carboxylate anion and a negatively charged counterion.

Another subset of compounds which is of interest is represented by formula I wherein one R group represents a —$C_{1-6}$ straight or branched chain alkyl group, substituted with one to four $R^d$ groups, wherein one $R^d$ group represents —R* or Q. Hence, a positively charged moiety —R* or Q is attached to an alkyl group.

Another subset of compounds which is of interest is represented by formula I wherein one R group represents a group without a positively charged moiety.

Another group of compounds of interest is represented by formula I wherein Q is selected from the group consisting of:

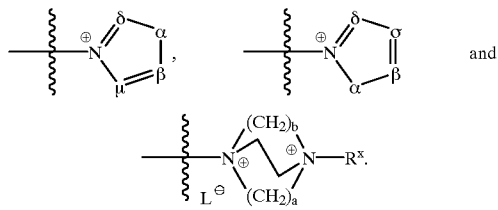

More particularly, the group of compounds which is of interest is represented by formula I wherein Q represents:

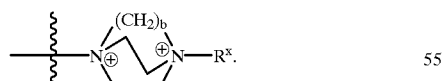

Within this subset of compounds, $L^-$, a and b are as originally defined, and $R^x$ is as originally defined, and represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups.

Another group of compounds of interest is represented by formula I wherein Q represents —$N^+R^xR^yR^z$, wherein $R^x$, $R^y$ and $R^z$ are as originally defined.

Another group of compounds of interest is represented by formula I wherein one R* group is present and is selected from:

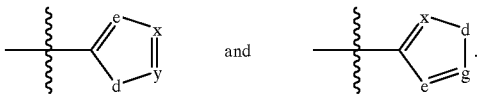

Within this subset, d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Another group of compounds of interest is represented by formula I wherein R is A—$(CH_2)_n$—Q, wherein A is O, S or $CH_2$, n is 0–3 and Q is as originally defined.

Another group of compounds of interest is represented by formula I wherein Z is trans-CH=CH and all other variables are as originally described.

Another group of compounds of interest is represented by formula I wherein X is iodine and all other variables are as originally described.

Another group of compounds of interest is represented by formula I wherein Z is —C≡C— and all other variables are as originally described.

A preferred subset of compounds of formula I which is of particular interest relates to compounds represented by formula Ia

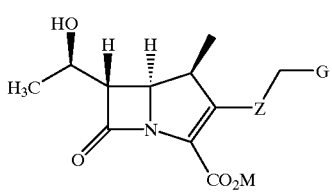

Ia wherein G is:

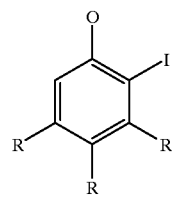

1

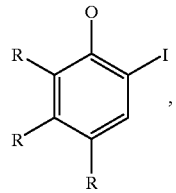

2

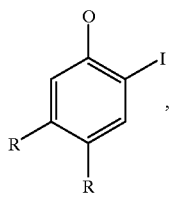
3

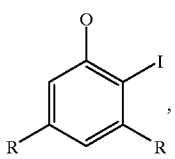
4

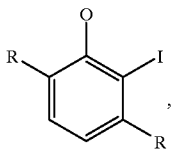
5

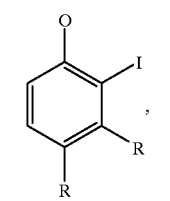
6

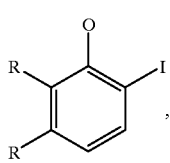
7

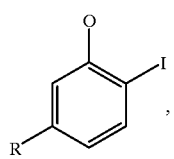
8

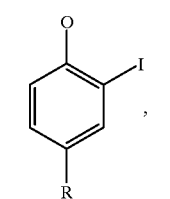
9

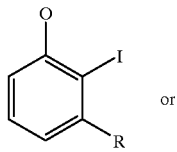
or

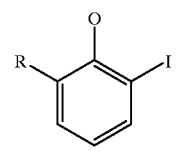

wherein:
Z is as originally described;
$CO_2M$ represents a carboxylate anion;
R group contains a positively charged moiety;
$R^d$ is as originally defined;
$R^h$ represents hydrogen or a $C_{1-6}$ straight or branched chain alkyl group;
Q is selected from the group consisting of:

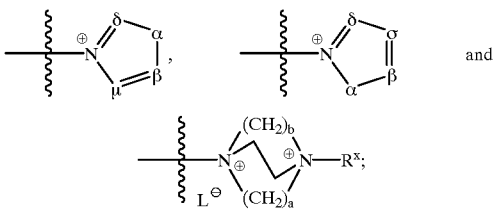

wherein $L^-$, a and b are as originally defined, and $R^x$ represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl or heteroaryl group being optionally substituted with from one to four $R^i$ groups or with one to two $C_{1-3}$ straight- or branched-chain alkyl groups, said alkyl groups being unsubstituted or substituted with one to four $R^i$ groups;
R* is selected from:

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Within this subset, all other variables are as originally defined with respect to formula I.

Another preferred subset of compounds of formula Ia is realized when G is 1, 3–4, 6, 8, 9 or 10, wherein R contains a positively charged moiety selected from the group consisting of: —R*, Q, A—$(CH_2)_n$—Q, and a $C_{1-6}$ straight or branched alkyl chain substituted with one $R^d$ group, wherein A is as originally described $R^d$ is independently selected —R* or Q;

Q is selected from the group consisting of:

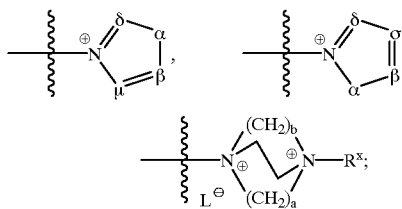 and

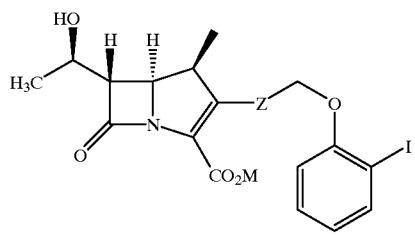

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

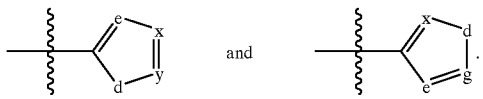

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

An even more preferred subset of formula Ia is realized when G is 8 or 9.

Another preferred subset of compounds is represented by formula Ib:

Ib

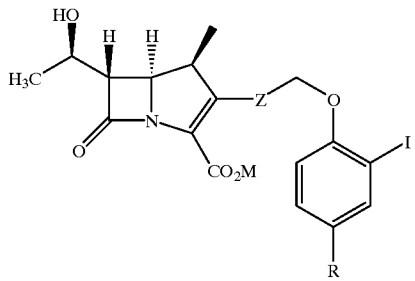

or a pharmaceutically acceptable salt thereof, wherein:

Z is as originally described;

$CO_2M$ represents a carboxylate anion;

Within this subset, all other variables are as originally defined with respect to formula I.

Another more preferred subset of compounds of the invention is represented by formula Ic:

Ic

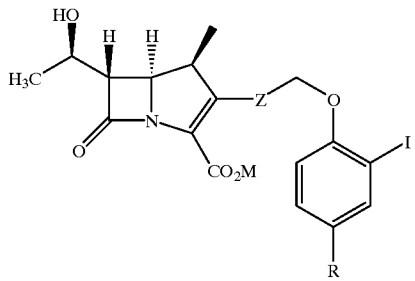

wherein:

R represents

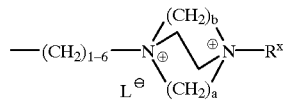

and $R^x$, a, b and $L^-$ are as originally defined.

Another more preferred subset of the compounds of formula Id is realized when:

R represents A—$(CH_2)_n$—Q, wherein A is O, S or $CH_2$, n is 0–3 and Q is selected from the group consisting of:

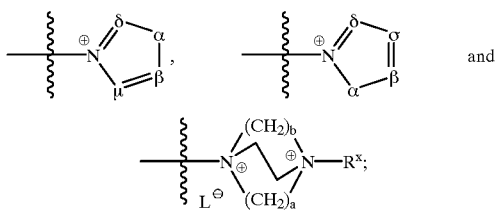

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups.

Within the subsets, all other variables are as originally defined with respect to formula I.

Representative examples of compounds of the invention are shown below. The invention is intended, where appropriate, to include protonated amines protonated at the appropriate pH, e.g., pH 7.

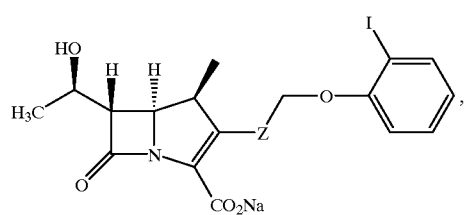
E-1
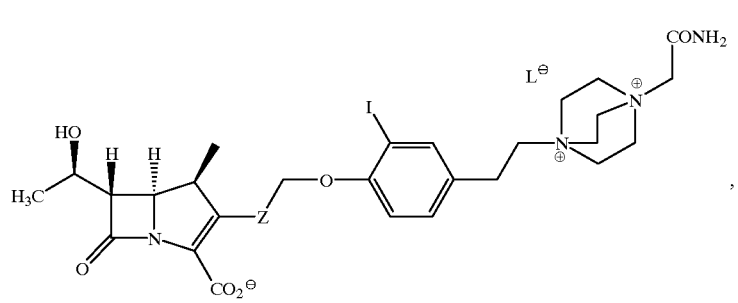
E-2
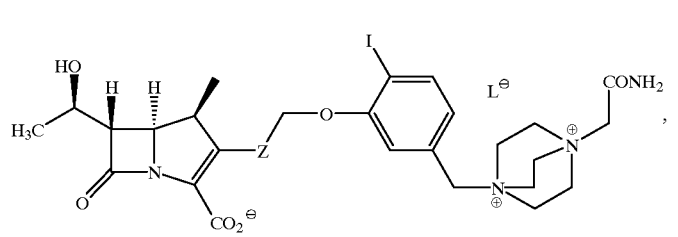
E-3
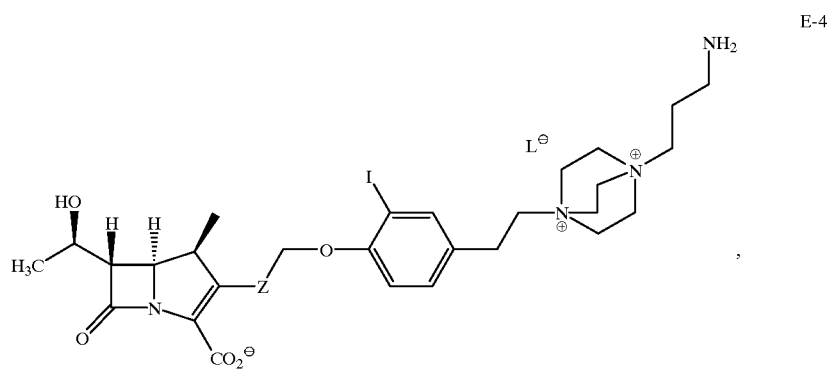
E-4
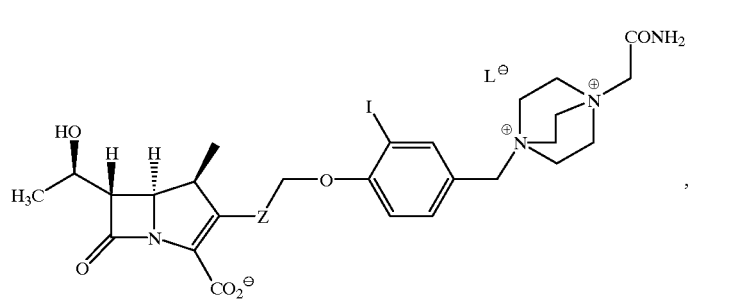
E-5

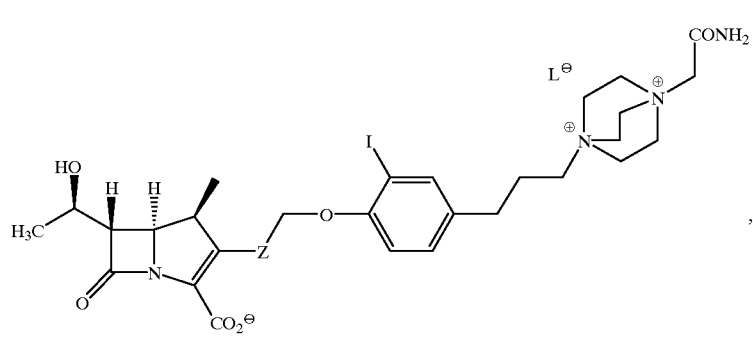
E-6
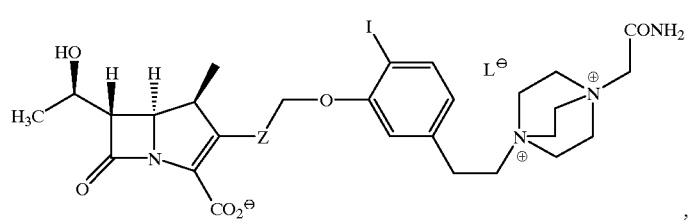
E-7
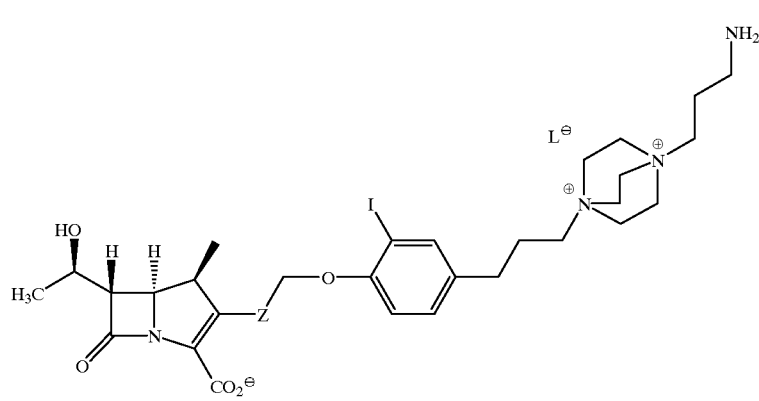
E-8
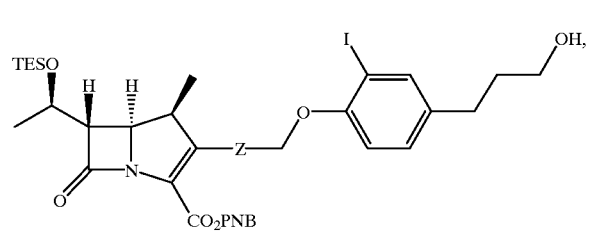
E9
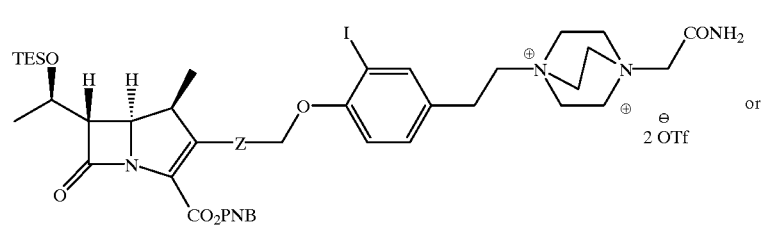
E10
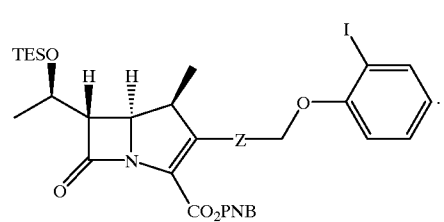
E11 or the pharmaceutically acceptable salts thereof.

The compounds of the present invention are prepared by two basic processes which are illustrated by the following generic schemes:

The compounds of the present invention are prepared as depicted in Flow sheets A and B. The vinyl linked carbapenems are prepared, as shown in Flow sheet A, by reacting a suitably protected, activated 2-triflyl-carbapen-2-em-3-carboxylate A1 with a hydroxy allylic trialkyl stannane, to produce A2, and then reacting the iodophenoxy under Mitsunobu conditions to produce A3. Removing any protecting groups which are present affords the desired final vinyllic product A4.

A5, deprotecting the propargylic hydroxy group to produce A6, and then reacting the iodophenoxy under Mitsunobu conditions to produce A7. Removing any protecting groups which are present affords the desired final acetylenic product A8.

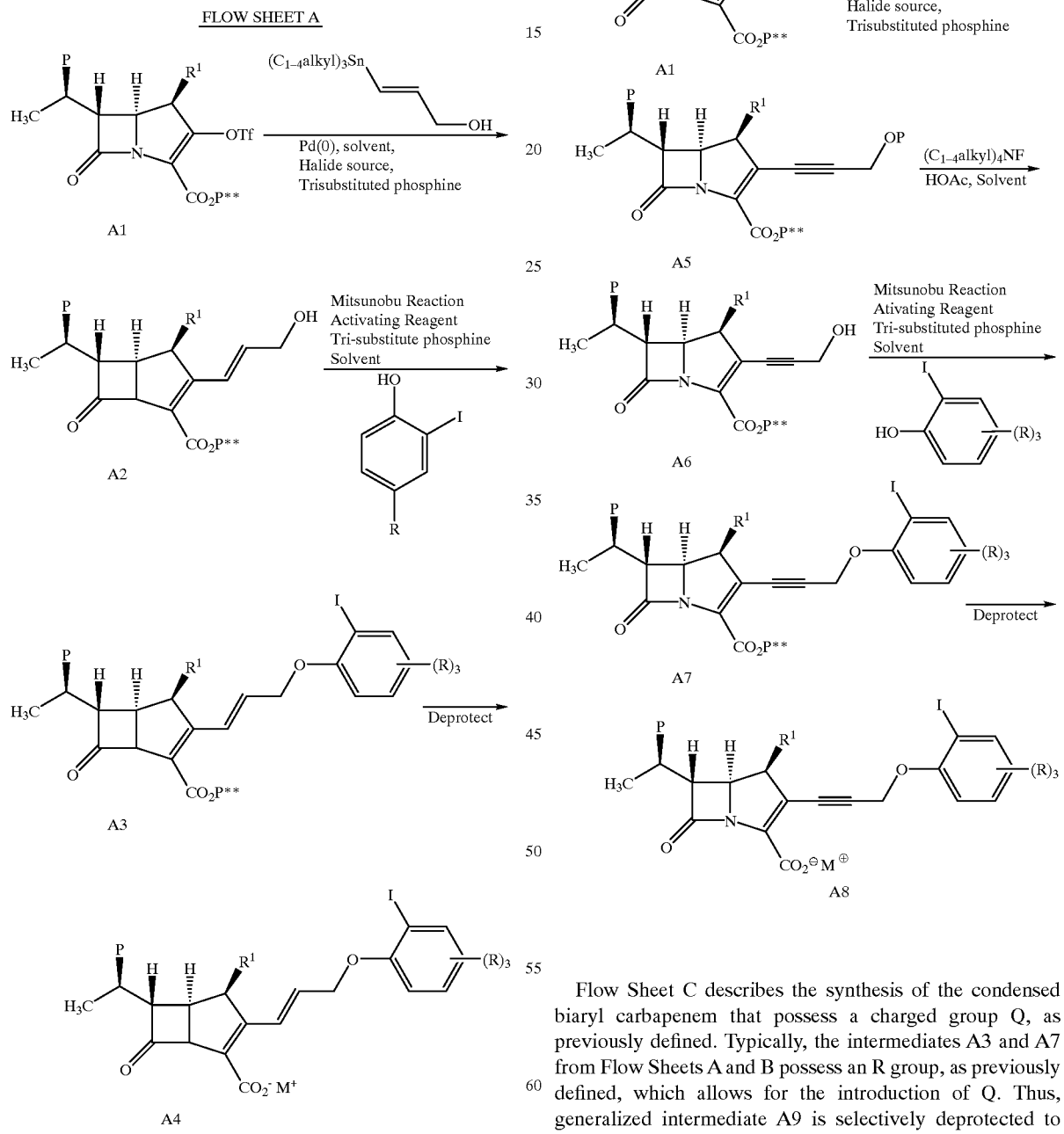

The acetylenic linked carbapenems are prepared as shown in Flow sheet B in which intermediate A1 is reacted with a protected hydroxy propargylic trialkyl stannane to produce Flow Sheet C describes the synthesis of the condensed biaryl carbapenem that possess a charged group Q, as previously defined. Typically, the intermediates A3 and A7 from Flow Sheets A and B possess an R group, as previously defined, which allows for the introduction of Q. Thus, generalized intermediate A9 is selectively deprotected to produce alcohol A10, which in term is activated for displacement with Q by conversion to intermediate A11. A11 is reacted with Q to form the quaternary ammonium intermediate A12. Removal of any protecting groups affords the final product A13.

FLOW SHEET C

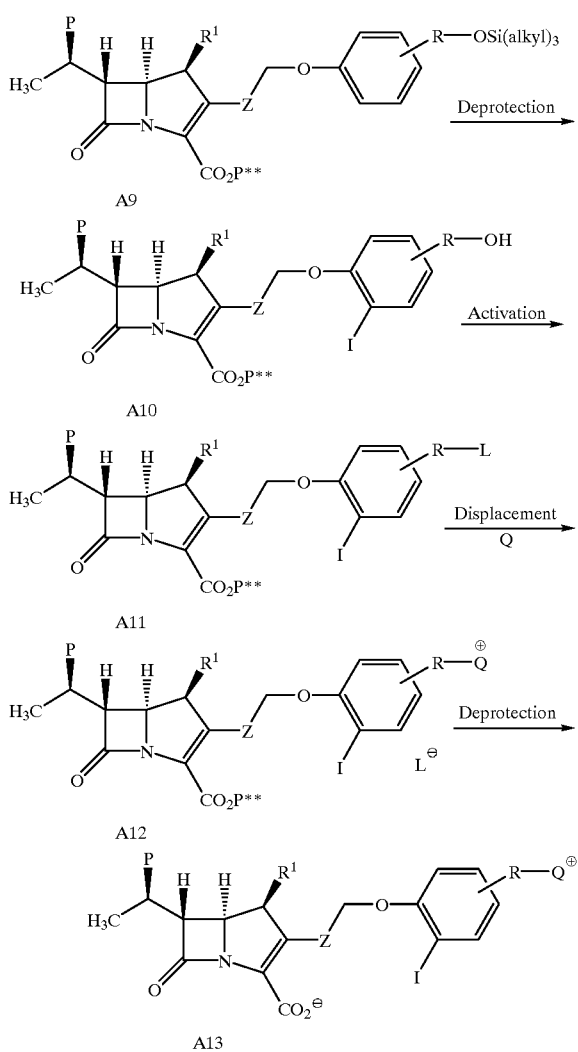

With reference to the flow sheets above, P, $R^1$, R, and M, are as defined with respect to the compounds of formula I, except that $M^+$ may be a metal cation, e.g., $Na^+$. See Dykstra, et al., Tet. Lett., 1998, 39, pg. 1865.

P** represents a carboxyl protecting group.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

PREPARATIVE EXAMPLE 1

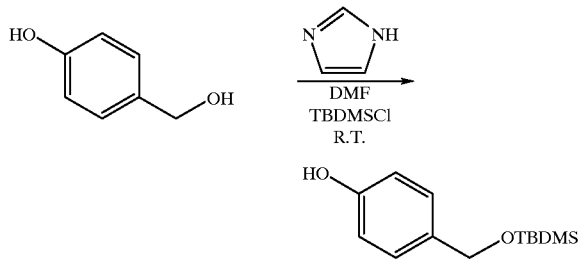

500 mg (4.03 mmoles) of commercially available 4-hydroxybenzyl alcohol was dissolved in 5.0 ml of anhydrous DMF, placed in an N2 atmosphere and chilled to 0° C. To the stirred DMF solution, 301 mg (4.33 mmoles) of imidazole was added followed by 604 mg (4.03 mmoles) of t-butyldimethylsilyl-chloride. The reaction was warmed to ambient temperature and stirred for 18 hrs.

The reaction mixture was extracted with ethyl acetate and partitioned with H$_2$O-dilute aq. sodium bicarbonate and sat. brine. The ethyl acetate extract was dried with anhydrous sodium sulfate and concentrated in vacuo to provide a viscous oil.

The crude product was purified via flash chrom. (230–400 mesh silica gel) and was eluted with a 4:1 mixture of hexanes:ethyl acetate to afford 908 mg of the silyl ether.

$^1$H NMR (CDCl$_3$) δ: 0.10 (s, 6H), 0.94 (s, 9H), 4.66 (s, 2H), 6.08 (s, 1H), 6.72 (d, J=7.5 Hz, 2H), 7.14 (d, J=8.7 Hz, 2H).

PREPARATIVE EXAMPLE 2

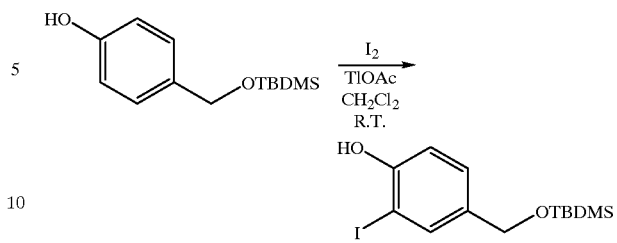

100 mg (0.418 mmoles) of the 4-hydroxy-silyl-ether was dissolved in 2.0 ml of sieve dried dichloromethane and placed in an N$_2$ atmosphere. To the stirred dichloromethane solution, 109 mg (0.418 mmoles) of thallium acetate was added and the tan suspension was stirred for 5 min. at ambient temperature. 109 mg (0.813 mmoles) of iodine was then added. The purple suspension was stirred for 2 hrs. and was filtered through a celite plug and was rinsed with 20 ml of ethyl acetate.

The ethyl acetate extract was partitioned with H$_2$O-ice and 5% aq. sodium thiosulfate and sat. brine. The extract was dried with andydrous sodium sulfate and concentrated in vacuo to provide 108 mg of a tan solid.

The crude product was purified using plate layer chromatography with a 4:1 hexanes:ethyl acetate eluent to provide 145 mg of the iodophenol.

$^1$H NMR (CDCl$_3$) δ: 0.07 (s, 6H), 0.90 (s, 9H), 4.60 (s, 2H), 5.18 (s, 1H), 6.91 (d, J=8.3 Hz, 1H), 7.15 (dd, J=1.9 Hz, 6.3 Hz, 1H), 7.58 (d, J=3.0 Hz, 1H).

PREPARATIVE EXAMPLE 3

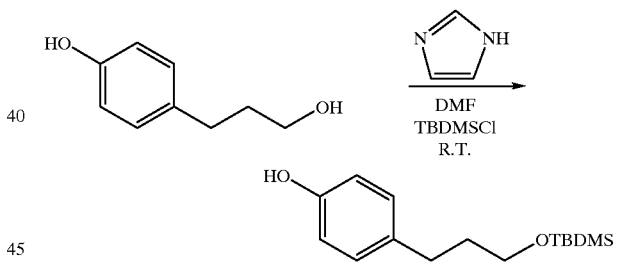

Using the analogous procedure of Preparative Example 1, the the carbinol was converted to the silyl ether in yield.

PREPARATIVE EXAMPLE 4

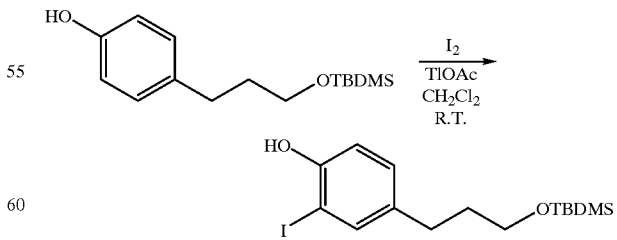

Using the analogous procedure of Preparative Example 2, the phenol was converted to the iodophenol.

$^1$H NMR (CDCl$_3$) δ: 0.06 (s, 6H), 0.91 (s, 9H), 1.68 (m, 2H), 2.55 (t, J=6.7 Hz, 2H), 3.58 (t, J=6.3 Hz, 2H), 5.22 (s,

1H), 6.88 (d, J=8.2 Hz, 1H), 7.05 (dd, J=2.0 Hz, 6.3 Hz, 1H), 7.48 (d, J=2.0 Hz, 1H).

PREPARATIVE EXAMPLE 5

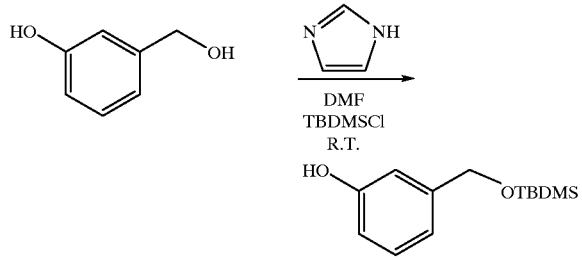

Using the analogous procedure of Preparative Example 1, the carbinol was converted to the silyl ether.

$^1$H NMR (CDCl$_3$) δ: 0.12 (s, 6H), 0.96 (s, 9H), 5.72 (s, 2H), 6.70 (dd, J=1.9 Hz, 4.7 Hz, 1H), 6.83–6.88 (m, 2H), 7.16 (t, J=7.7 Hz, 1H).

PREPARATIVE EXAMPLE 6

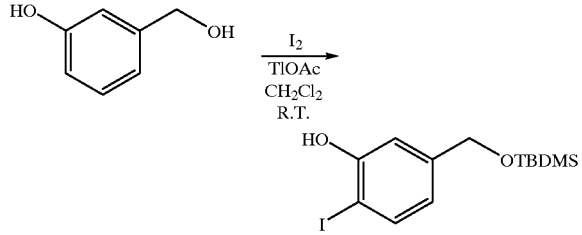

Using the analogous procedure of Preparative Example 2, the phenol was converted to the iodophenol.

$^1$H NMR (CDCl$_3$) δ: 0.10 (s, 6H), 0.94 (s, 9H), 4.66 (s, 2H), 5.29 (s, 1H), 6.66 (dd, J=1.9 Hz, 4.7 Hz, 1H), 6.97 (d, J=2.0 Hz, 1H), 7.56 (d, J=7.3 Hz, 1H).

PREPARATIVE EXAMPLE 7

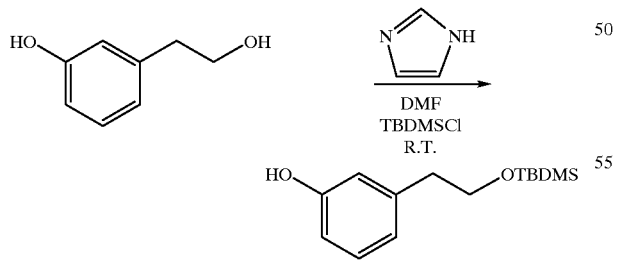

Using the analogous procedure of Preparative Example 1, the carbinol was converted to the silyl ether.

$^1$H NMR (CDCl$_3$) δ: 0.08 (s, 6H), 0.88 (s, 9H), 2.76 (t, J=7.2 Hz, 2H), 3.78 (t, J=7.2 Hz, 2H), 6.65–6.69 (m, 2H), 6.76 (d, J=7.4 Hz, 1H), 7.12 (t, J=6.5 Hz, 1H).

PREPARATIVE EXAMPLE 8

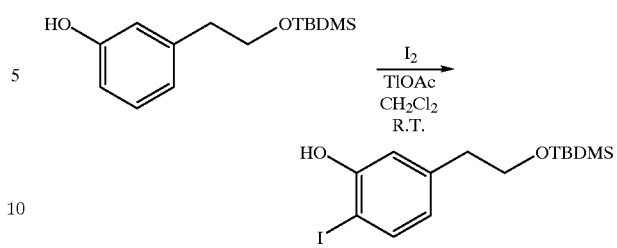

Using the analogous procedure of Preparative Example 2, the phenol was converted to the iodophenol.

$^1$H NMR (CDCl$_3$) δ: 0.10 (s, 6H), 0.88 (s, 9H), 2.72 (t, J=7.0 Hz, 2H), 3.77 (t, J=6.9 Hz, 2H), 5.49 (s, 1H), 6.53 (dd, J=2.0 Hz, 6.1Hz, 1H), 6.89 (d, J=2.0 Hz, 1H), 7.52 (d, J=8.0 Hz, 1H).

PREPARATIVE EXAMPLE 9

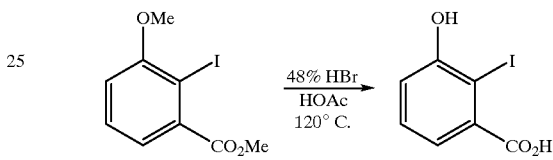

500 mg (1.712 mmoles) of the methyl ester (Stanley, W., M.; McMahan, E.; Adams, R. *JACS*, 1933, 55, 706) was dissolved in 2.9 ml of 48% HBr and 1.49 ml of acetic acid and was placed in an N$_2$ atmosphere. The reaction was stirred for 4 hrs. at 120° C. The cooled reaction mixture was basified to pH 10.0 with 2 ml of 5N aq. sodium hydroxide and partitioned with ethyl acetate-H$_2$O and ice. The aq. layer was saved and acidified to pH 2.5 with 2.0 N aq. hydrochloric acid, forming a white solid that precipitated from solution. The solid was collected in a sintered glass funnel, washed with 10 ml of deionized H$_2$O and dried in vacuo to provide 286 mg of benzoic acid.

$^1$H NMR (d$_6$-Me$_2$CO) δ: 7.06 (m, 1H), 7.29 (t, J=8.0 Hz, 1H), 7.51 (dd, J=1.5 Hz, 5.9 Hz, 1H).

PREPARATIVE EXAMPLE 10

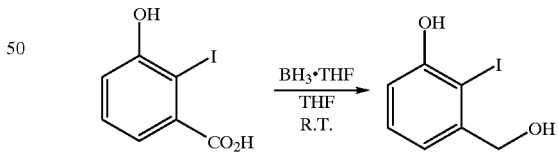

286 mg (1.08 mmoles 0 of benzoic acid was dissolved in 5.0 ml of anhydrous THF and was placed in an N$_2$ atmosphere. To the stirred THF solution, 2.16 ml of borane-THF complex was added dropwise over 20 min. and the reaction was stirred for 2 hrs. at ambient temperature. 10 ml of methanol was then added to the THF solution slowly over 1 hr.

The reaction was extracted with ethyl acetate and partitioned with H$_2$O-ice and sat. brine. The ethyl acetate extract was dried with anhydrous sodium sulfate and concentrated in vacuo to dryness. The crude product was purified using silica gel plate layer chromatography eluted with a 7:3 ethyl acetate:hexanes mixture to afford 120 mg of the benzyl alcohol.

PREPARATIVE EXAMPLE 11

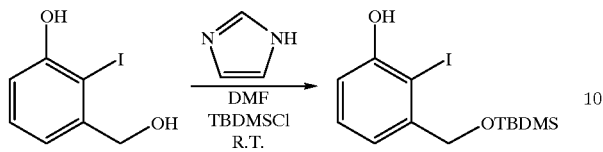

Using the analogous procedure of Preparative example 1, the carbinol was converted to the silyl ether.

0.10 (s, 6H), 0.95 (s, 9H), 4.70 (s, 2H), 4.94 (s, 1H), 6.68 (dd, J=2.3 Hz, 5.5 Hz, 1H), 6.83 (m, 1H), 7.16 (t, J=7.8 Hz, 1H).

PREPARATIVE EXAMPLE 12

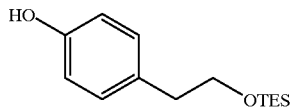

To a stirred solution of commercially available 2-(4-hydroxyphenyl)ethanol (3.0 g, 21.7 mmoles), in 30 ml of sieve dried N,N-dimethyformamide, at 0° C., was added imidazole (1.64 g, 23.9 mmoles) followed by neat triethyl-silyl triflate (5.4 ml, 23.9 mmoles). The resulting solution was warmed to ambient temperature and was stirred for 18 hrs. The reaction mixture was diluted with ethyl acetate, washed with cold 1.0N aq. HCl, conc. aq. sodium bicarbonate and sat. brine. The organic phase was dried over anhydrous sodium sulfate, filtered and concentrated in vacuo to give a colorless oil. Flash chromatography (50:1 $SiO_2$: prod., eluent: 4:1 hexanes:ethyl acetate) gave 2.7 g (49%) of a colorless oil.

$^1$H NMR (CDCl$_3$) δ: 0.62 (q, 6H), 0.95 (t, 9H), 2.82 (t, 2H), 3.80 (t, 2H), 6.25 (s, 1H), 7.05 (d, 2H), 7.75 (d, 2H).

PREPARATIVE EXAMPLE 13

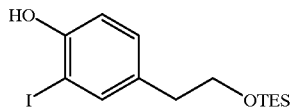

To a stirred solution of (2.0 g, 7.91 mmoles) the product obtained in preparative example 12, in 30 ml of dichloromethane, at ambient temperature, was added (2.08 g, 7.91 mmoles) of thallium (I) acetate in portions. After stirring the suspension for 5 min., iodine (4.0 g, 15.81 mmoles) was added and the mixture was stirred for 2.5 hrs. The resulting slurry was diluted with diethyl ether and filtered through celite. The filtrate was washed with water-ice, 5% aq. sodium thiosulfate and sat. brine. The orgainic phase was dried over anhydrous sodium sulfate and concentrated in vacuo to give a tan solid. Flash chromatography (100:1 $SiO_2$: product, eluent: 4:1 hexanes:ethyl acetate) gave 744 mg (27%) of the product as a crystalline solid; $^1$H NMR (CDCl$_3$) δ: 0.08 (t, 9H), 2.75 (t, 2H), 3.75 (t, 2H), 5.25 (s, 1H), 7.18 (dd, 1H), 7.52 (d, 1H) and 363 mg (17.4%) of the 4-hydroxethyl-2-iodophenol, shown below, as a tan solid; $^1$H NMR (CDCl$_3$) δ: 2.78 (t, 2H), 3.76 (t, 2H), 6.89 (d, 1H), 7.05 (dd, 1H), 7.55 (d, 1H).

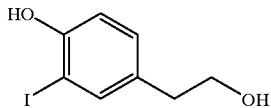

PREPARATIVE EXAMPLE 14

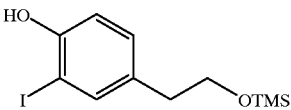

To a stirred solution of (121 mg, 0.458 mmoles) the 4-hydroxethyl-2-iodophenol obtained in preparative example 13, in 2.0 ml of sieve dried N,N-dimethylformamide, at 0° C., was added imidazole (34 mg, 0.504 mmoles) followed by neat trimethylsilyl chloride (0.057 ml, 0.504 mmoles). The cooling bath was removed and the solution was stirred at ambient temperature for 18 hrs. The mixture was diluted with ethyl acetate, washed with water, conc. aq. sodium bicarbonate and sat. brine. The organic phase was dried over anhydrous sodium sulfate and concentrated in vacuo to provide 153 mg (100%) of a white crystalline solid.

$^1$H NMR (CDCl$_3$) 67 : 0.08 (t, 9H), 2.75 (t, 2H), 3.75 (t, 2H), 5.25 (s, 1H), 7.18 (dd, 1H), 7.52 (d, 1H).

PREPARATIVE EXAMPLE 15

To a stirred solution of commercially available propargyl alcohol (5.0 g, 35.72 mmoles) in 50 ml of sieve dried N,N-dimethylformamide, cooled to 0° C., was added imidazole (668 mg, 9.83 mmoles) followed by neat triethylsilyl chloride (16.2 ml, 96.21 mmoles). The cooling bath was removed and the mixture was stirred at ambient temperature for 10 min. The resulting solution was diluted with ethyl acetate, washed with water-ice, 0.5M aq. sodium bicarbonate and saturated brine. The organic phase was dried over anhydrous sodium sulfate, filtered and concentrated in vacuo to give a colorless oil. Fractional distillation gave 3.03 g (51%) (b.p. 57° C.–61° C., 3.7 mm); of pure product as a colorless oil.

$^1$H NMR (CDCl$_3$) δ: 0.65 (q, 6H), 0.95 (t, 9H), 2.43 (t, 1H), 4.35 (dd, 2H).

PREPARATIVE EXAMPLE 16

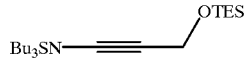

To a stirred solution of product obtained in preparative example 15 (3.03 g, 18.15 mmoles), in 30 ml of THF, cooled to −78° C., was added n-butyllithium (8.0 ml, 19.96 mmoles) dropwise over 30 min. The reaction was allowed to warmed to −20° C. and was stirred for 1 hour. Neat tri-n-butyltin chloride (5.89 ml, 21.78 mmoles) was then added dropwise over 30 min. The reaction mixture was warmed to 0° C. and stirred for 1 hr. The resulting dark solution was diluted with ethyl acetate, washed with water-ice and sat. brine. The organic phase was dried over anhydrous sodium sulfate, filtered and concentrated in vacuo to give a brown oil. Flash chromatography with 200–400 mesh florisil (100:1 florisil: product, eluent: 9:1 hexanes:dichloromethane) gave 6.12 g (74%) of the product as a colorless oil.

$^1$H NMR (CDCl$_3$) δ: 0.64 (q, 6H), 0.91 (t, 6H), 1.02 (t, 18H), 1.31 (m, 6H), 1.72 (m, 6H), 4.34 (s, 2H).

EXAMPLE 1

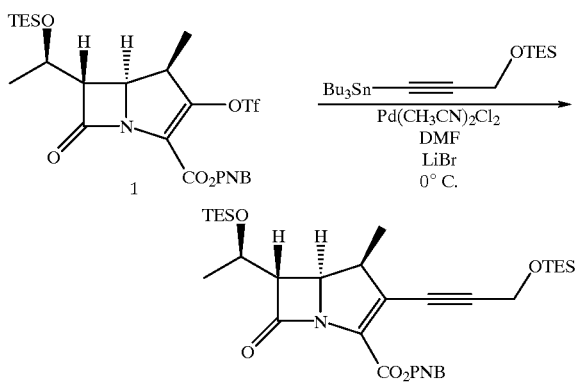

To a stirred solution of carbapenem 2-yl-triflate 1 (100 mg, 0.164 mmoles) and propargylstannane (112 mg, 0.246 mmoles) obtained in preparative example 16, in 2 mL of anhydrous N,N-dimethylformamide, at 0° C., was added lithium bromide (28 mg, 0.328 mmoles) and bis-acetonitrilepalladium(II) chloride (2.1 mg, 0.0082 mmoles). The reaction mixture was stirred for 1 hr, diluted with ethyl acetate and washed with water-ice and saturated brine. The organic phase was dried over anhydrous sodium sulfate, filtered and concentrated in vacuo to give an orange oil. Silica gel plate layer chromatography (2×1000 microns; eluent: 4:1 hexane ethyl acetate) gave 70 mg (68%) of the desired product as a pale yellow oil.

$^1$H NMR (CDCl$_3$) δ: 0.59 (m, 12H), 0.73 (m, 18H), 1.24 (d, 3H), 1.26 (d, 3H), 3.18 (m, 1H), 3.20 (dd, 1H), 4.12 (d, 1H), 4.25 (dd, 1H), 4.53 (s, 2H), 5.28–5.49 (q, 2H), 7.65 (d, 2H), 8.21 (d, 2H).

EXAMPLE 2

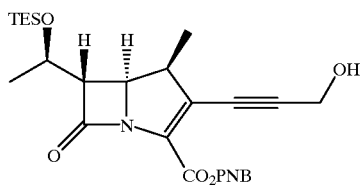

To a stirred solution of (77 mg, 0.122 mmoles) the product obtained in example 1, in 1.0 ml of anhydrous THF, at 0° C., was added sequentially acetic acid (11 ml, 0.183 mmoles) and a 1.0 M THF solution of tetra-butylammonium fluoride (0.122 ml, 0.122 mmoles). The mixture was stirred for 1 hr., diluted with ethyl acetate, washed with water, saturated aq. sodium bicarbonate and saturated brine. The organic phase was dried over sodium sulfate, filtered and concentrated in vacuo to give a yellow solid. Silica gel plate layer chromatography (1×1000 microns; eluent: 1:1 hexanes:ethyl acetate) gave 33 mg (53%) of a yellow crystalline solid.

$^1$H NMR (CDCl$_3$) δ: 0.57 (q, 6H), 0.90 (t, 9H), 1.22 (t, 6H), 1.74 (t, 1H), 3.16 (m, 1H), 3.23 (dd, 1H), 4.23–4.32 (m, 2H), 4.48 (d, 2H), 5.26–5.48 (q, 2H), 7.64 (d, 2H), 8.21 (d, 2H).

EXAMPLE 3

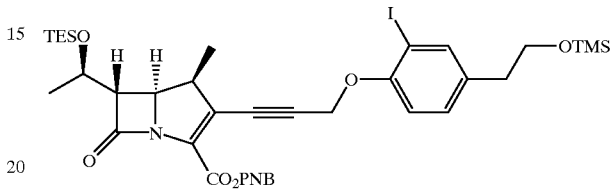

The product (82 mg, 0.159 mmoles) obtained from example 2 along with the product (58 mg, 0.179 mmoles) obtained in example 7 and triphenylphosphine (46 mg, 0.179 mmoles) were combined, in 2.0 ml of anhydrous THF and cooled to 0° C. Neat diisopropylazodicarboxylate (0.035 ml, 0.179 mmoles) was added and the mixture was stirred for 20 min. The resulting solution was concentrated in vacuo to give an orange oil. Silca gel plate layer chromatography (1×1000 microns; eluent: 4:1 hexanes:ethyl acetate) gave 66 mg (56%) of a yellow oil.

$^1$H NMR (CDCl$_3$) δ: 0.1 (s, 9H), 0.63 (q, 6H), 0.89 (t, 9H), 1.14 (d, 3H), 1.25 (d, 3H), 2.75 (m, 2H), 3.15 (m, 1H), 3.3 (m, 1H), 3.75 (t, 2H), 4.25 (m, 2H), 4.91 (s, 2H), 5.35 (ABq, 2H), 6.95 (m, 1H), 7.15 (dd, 1H), 7.62 (m, 3H), 8.21 (d, 2H).

EXAMPLE 4

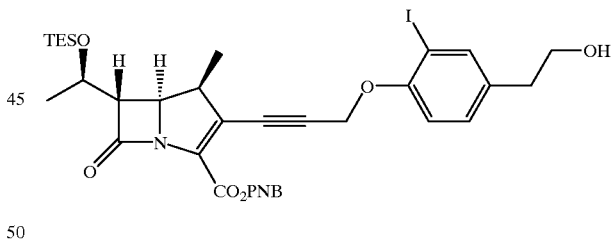

To a stirred solution of (66 mg, 0.0896 mmoles) the product obtained in example 3, in 1.0 ml of anhydrous THF, cooled to 0° C., was added sequentially acetic acid (0.0076 ml, 0.134 mmoles) and a 1.0 M THF solution of tetra-butylammonium fluoride (0.089 ml, 0.089 mmoles). The mixture was stirred for 1 hr., diluted with ethyl acetate, washed with water-ice, saturated aq. sodium bicarbonate and sat. brine. The organic phase was dried over anhydrous sodium sulfate, filtered and concentrated in vacuo to provide a colorless oil. Flash chrom. (50:1 SiO$_2$: product, eluent: 1:1 hexanes:ethyl acetate) gave 49 mg (72%) of a tan solid.

$^1$H NMR (CDCl$_3$) δ: 0.55 (q, 6H), 0.95 (t, 9H), 1.15 (d, 3H), 1.25 (d, 3 H), 2.78 (t, 2H), 3.18 (m, 1H), 3.32 (dd, 1H), 3.85 (bt, 3H), 4.25 (d, 1H), 4.28 (dd, 1H), 4.9 (s, 2H), 5.3 (ABq, 2H), 6.92 (d, 1H), 7.15 (dd, 1H), 7.58 (d, 1H), 7.65 (dd, 1H), 8.18 (d, 1H).

EXAMPLE 5

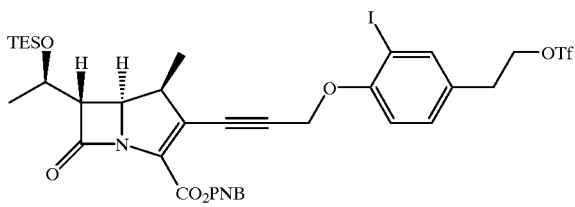

To a stirred solution of (49 mg, 0.0645 mmoles) the product obtained in example 4, in 1.0 ml of anhydrous THF, cooled to −20° C., was added neat 2,6-lutidine (0.0079 ml, 0.0678 mmoles) and the solution was stirred for 5 min. Neat triflic anhydride (0.012 ml, 0.0710 mmoles) was then added and the mixture was stirred for 15 min. The reaction mixture was diluted with ethyl acetate, washed with water-ice, 0.050 ml of 2.0N aq. HCl and saturated brine. The organic phase was dried over anhydrous sodium sulfate, filtered and concentrated in vacuo to give 57 mg (100%) of the desired product which was used without purification.

EXAMPLE 6

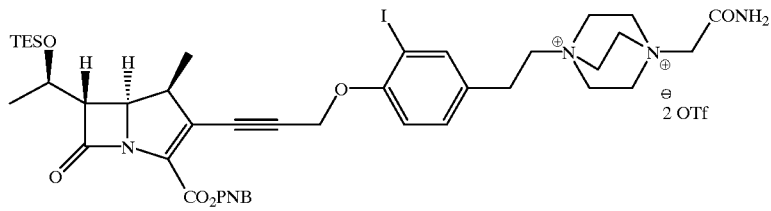

To a stirred solution of (57 mg, 0.0645 mmoles) freshly prepared product obtained from example 5, in 1.0 ml of sieve dried acetonitrile, at ambient temperature, was added 4-carbamoylmethyl-1,4-diazoniabicyclo-{2.2.2}-octyl triflate (21 mg, 0.0645 mmoles). The solution was stirred for 30 min., concentrated in vacuo to dryness and redissolved in 1.0 ml of acetone. The solution was diluted with 8.0 ml of diethyl ether to give a milky suspension which was centrifuged and dried to give 53 mg (76%) of a semi-pure amorphous solid.

$^1$H NMR (CD$_6$CO) δ: 0.58 (q, 6H), 0.93 (t, 9H), 1.21 (m, 6H), 3.28 (m, 1H), 3.35 (m, 2H), 3.58 (t, 1H), 4.02 (m, 2H), 4.20 (s, 2H), 4.31 (m, 1H), 4.44 (dd, 1H), 4.47 (bt, 6H), 4.65 (s, 2H), 5.09 (s, 2H), 5.29–5.47 (ABq, 2H), 7.11 (d, 2H), 7.29 (bs, 1H), 7.41 (dd, 1H), 7.72 (bs, 1H), 7.78 (d, 2H), 7.82 (d, 1H), 8.21(d, 1H).

EXAMPLE 7

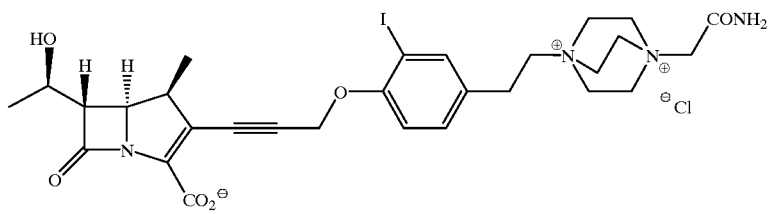

To a stirred solution of (35 mg, 0.0292 mmoles) the product obtained in example 6, in a 2:1 mixture of THF:H$_2$O, cooled to 0° C., was added 1.0 N aq. HCl (0.029 ml, 0.029 mmoles). The cooling bath was removed and the reaction was stirred at ambient temperature for 1.5 hrs. The mixture was cooled to 0° C. and neutralized with 1.0N aq. sodium bicarbonate (0.029 ml, 0.029 mmoles). 5% Pt/C (3.5 mg) catalyst was then added and the mixture was stirred vigorously, in an atmosphere of hydrogen, at ambient temperature and pressure for 22 min. The reaction mixture was filtered through celite and concentrated in vacuo to give a tan residue which was redissolved in 2.0 ml of deionized water. The aq. solution of crude product was passed through a column containing Macro prep ion exchange resin and was eluted with a 5% aq. brine solution and was subsequently desalted using amberchrom CG-161 resin to give after lyophilization 15.8 mg (79%) of a white solid.

1H NMR (2:1 D$_2$O: CD$_3$CN) δ: 1.22 (d, 3H), 1.41 (d, 3H), 3.22 (m, 3H), 3.56 (dd, 1H), 3.92 (m, 2H), 4.22 (bt, 6H), 4.34 (m, 2H) 4.44 (bt, 6H), 4.60 (S, 2H), 5.25 (S, 2H), 7.34 (d, 1H), 7.53 (d, 1H), 8.05 (s, 1H).

EXAMPLE 8

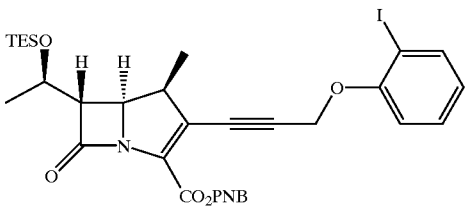

Using the procedure described in example 3, a mixture of (70 mg, 0.136 mmoles) the product obtained in example 2,2-iodophenol (36 mg, 0.163 mmoles) and triphenylphosphine (43 mg, 0.163 mmoles) is combined and dissolved in 1.0 ml of anhydrous THF. The solution is cooled to 0° C., treated with diisopropylazodicarboxylate (0.032 ml, 0.163 mmoles) and stirred for 20 min. Purification by silica gel plate layer chromatography yields the product.

EXAMPLE 9

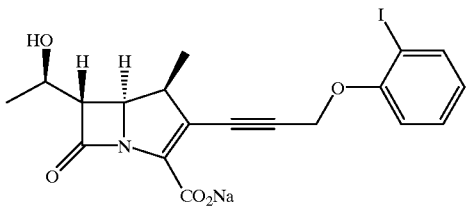

Using the procedure described in example 7, the (82 mg, 0.114 mmoles) product obtained in example 8, in 1.0 ml of a 2:1 THF: water solution, is treated with 1.0 N aq. HCl (0.114 ml, 0.114 mmoles) and stirred at ambient temperature for 1.5 hrs. The resulting solution is cooled to 0° C. and basicified with 1.0N aq. sodium bicarbonate (0.228 ml, 0.228 mmoles). Catalytic reduction using 5% Pt/C catalyst at atmospheric pressure in a hydrogen atmosphere followed by purification with amberchrom CG-161 resin gives after lyophilization the desired product.

EXAMPLE 10

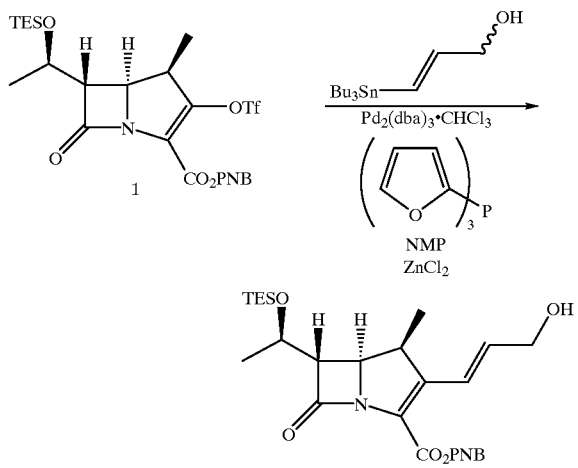

A mixture of 2-yl-carbapenem triflate 1 (200 mg, 0.329 mmoles), a 2:1 mixture of (E)-trans: (Z)-cis vinylstannanes (0.144 ml 0.493 mmoles), prepared as described in Jung, M. E.; Light, L. A. *Tetrahedron Lett.* 1982, 23, 3851, palladium dibenzylidineacetone chloroform complex (17 mg, 0.0165 mmoles) and tris-trifuryl phosphine (7.6 mg, 0.0329 mmoles) was combined and dissolved in 4.0 ml of N-methylpyrrolidinone, at ambient temperature. A 1.0 M etheral solution of zinc chloride (0.0329 ml, 0.0329 mmoles) was then added to the solution and the mixture was stirred for 6 hrs. The mixture was diluted with ethyl acetate, washed with water-ice and sat. brine. The organic phase was dried over anhydrous sodium sulfate, filtered and conc. in vacuo to give a brown oil. Silica gel plate layer chromatography (4×1000 microns, eluent: 1:1 ethyl acetate:hexanes) yielded 103 mg (60%) of the desired product as a colorless oil.

$^1$H NMR (CDCl$_3$) δ: 0.58 (m, 6H), 0.94 (t, 9H), 1.22 (d, 3H), 1.29 (d, 3H), 3.23 (dd, 1H), 3.37 (d, 1H), 4.19 (dd, 1H), 4.21 (m, 1H), 4.32 (dd, 2H), 5.26–5.48 (q, 2H), 6.18 (dd, 1H), 7.27 (d, 1H), 7.68 (d, 2H), 8.22 (d, 2H).

EXAMPLE 11

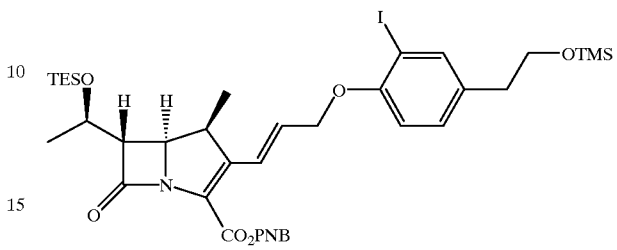

Using the procedure described for example 3, the (113 mg, 0.218 mmoles) product obtained in example 10 along with the (81 mg, 0.241 mmoles) product obtained in example 7 and triphenylphosphine (63 mg, 0.241 mmoles) is combined and dissolved in 2.0 ml of anhydrous THF. The stirred solution is cooled to 0° C. and treated with diisopropylazodicarboxylate (0.048 ml, 0.241 mmoles). Purification by silca gel plate layer chromatography (1×1000 microns; eluent: 4:1 hexanes:ethyl acetate) provides the product.

EXAMPLE 12

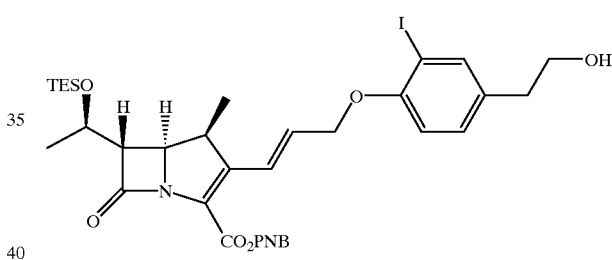

Using the procedure described in example 4, the (91 mg, 0.123 mmoles) product obtained in example 11, in 1.0 ml of anhydrous THF, is treated sequentially with acetic acid (0.0010 ml, 0.185 mmoles) and a 1.0 M THF solution of tetra-butylammonium fluoride (0.136 ml, 0.136 mmoles). Silica gel chromatography yields the depicted product.

EXAMPLE 13

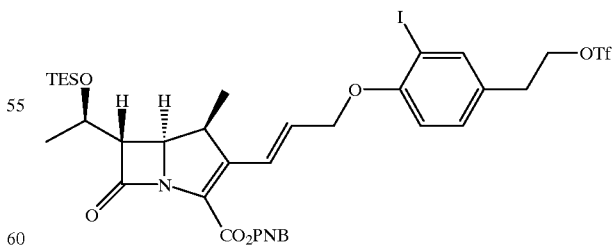

Using the procedure described in example 5, the (59 mg, 0.079 mmoles) product obtained in example 13, in 1.0 ml of anhydrous THF, is treated with neat 2,6-lutidine (0.011 ml, 0.0931 mmoles) and neat triflic anhydride (0.016 ml, 0.0975 mmoles) to give the desired product.

EXAMPLE 14

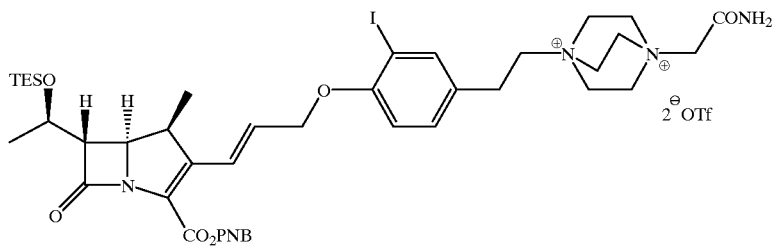

Using the procedure described in example 6, the (70 mg, 0.079 mmoles) product obtained from example 13, in 1.0 ml of sieve dried acetonitrile, is reacted with 4-carbamoylmethyl-1,4-diazoniabicyclo-{2.2.2}-octyl triflate (25 mg, 0.079 mmoles). The desired product is precipitated from a solution of acetone/ether to give the product.

EXAMPLE 15

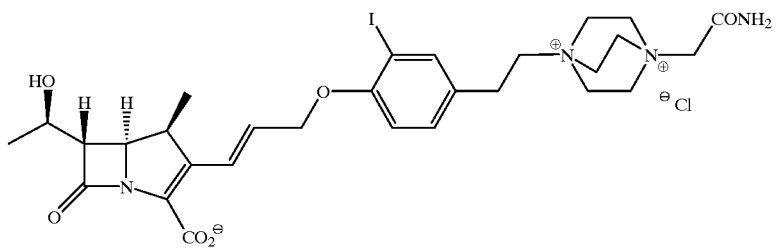

Using the procedure described in example 7, the (73 mg, 0.060 mmoles) product obtained in example 14 in a 2:1 mixture of THF: $H_2O$, cooled to 0° C., is treated with 1.0N aq. HCl (0.060 ml, 0.060 mmoles) and stirred at ambient temperature for 1.5 hrs. The resulting solution is cooled to 0° C. and basicified with 1.0N aq. sodium bicarbonate (0.060 ml, 0.060 mmoles). The mixture is catalytically hydrogenated with 5% Pt/C (6.7 mg) catalyst to provide the crude residue which is treated with Macro prep ion exchange resin and is desalted with amberchrom CG-161 resin to give after lyophilization 19 mg (44%) of the desired product.

EXAMPLE 16

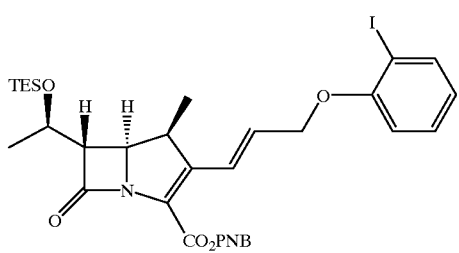

Using the procedure described in example 3, a mixture of (57 mg, 0.110 mmoles) the carbinol obtained in example 10, 2-iodophenol (29 mg, 0.132 mmoles) and triphenylphosphine (35 mg, 0.132 mmoles) is combined and dissolved in 1.0 ml of anhydrous THF. The stirred solution is cooled to 0° C. and treated with diisopropylazodicarboxylate (0.026 ml, 0.132 mmoles). Silica gel plate layer chromatography yields the desired product.

EXAMPLE 17

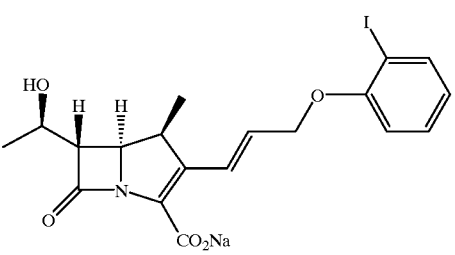

Using the procedure described in example 7, the (59 mg, 0.081 mmoles) product obtained in example 16, in 1.0 ml of a 2:1 THF: water solution, is treated with 1.0N aq. HCl (0.081 ml, 0.081 mmoles) and stirred at ambient temperature for 1.5 hrs. The resulting solution is cooled to 0° C. and basicified with 1.0N aq. sodium bicarbonate (0.162 ml, 0.162 mmoles). The mixture is catalytically hydrogenated using 5% Pt/C (5.9 mg) catalyst followed by purification with amberchrom CG-161 resin to give after lyophiliztion the desired product.

What is claimed is:

1. A compound represented by formula I:

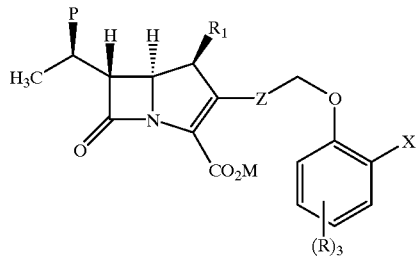

or a pharmaceutically acceptable salt thereof, wherein:

$R^1$ represents H or methyl;

$CO_2M$ represents a carboxylic acid, a carboxylate anion, or a pharmaceutically acceptable ester group, provided that when $CO_2M$ represents a carboxylate anion it is balanced by Q;

X represents a halogen selected from the group consisting of iodine, bromine, chlorine or fluorine;

P represents hydrogen, hydroxyl, or F;

Z represents trans-ethenediyl or ethynediyl;

each R is independently selected from: —R*; —Q; hydrogen; halo; —CN; —$NO_2$; —$NR^aR^b$; —$OR^c$; —$SR^c$; —$C(O)NR^aR^b$; —$C(O)OR^h$; —$S(O)R^c$; —$SO_2R^c$; —$SO_2NR^aR^b$; —$NR^aSO_2R^b$; —$C(O)R^a$; —$OC(O)R^a$; —$OC(O)NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; —$C_{3-7}$ cycloalkyl, unsubstituted or substituted with one to four $R^d$ groups and A—$(CH_2)_n$—Q, wherein A is O, S, or $CH_2$, and n is 0–3;

each $R^a$, $R^b$ and $R^c$ independently represents hydrogen, —R*, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

$R^e$, $R^f$ and $R^g$ represent hydrogen; —R*; —$C_{1-6}$ straight- or branched-chain alkyl, unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; $NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl, Q is selected from the group consisting of:

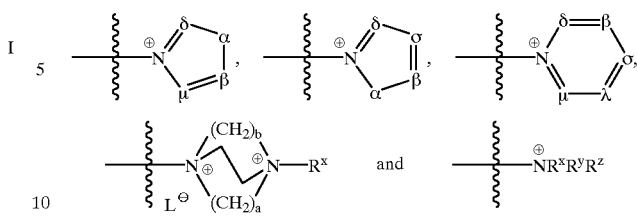

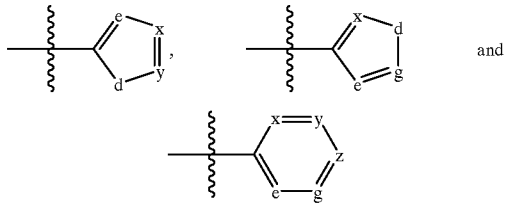

wherein:

a and b are 1, 2 or 3;

$L^-$ is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

R* is selected from the group consisting of:

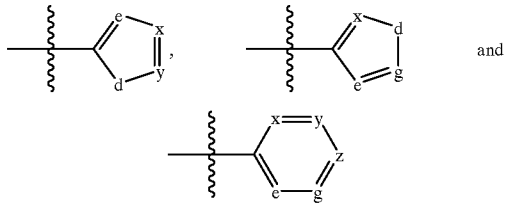

wherein:

d represents O, S or $NR^k$;

e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_n$Q where n=1, 2 or 3 and Q is as previously defined;

each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^h$; — $NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a $C_{1-8}$ straight- or branched-chain alkyl, optionally interrupted by one or two of O, S, SO, $SO_2$, NRW, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four Ri groups or with one to two $C_{1-3}$ straight- or branched-chain alkyl groups, said alkyl groups being unsubstituted or substituted with one to four Ri groups; and $R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

Wherein the molecule contains no more than two cations balanced by a carboxylate anion and a negatively charged pharmaceutically acceptable counterion.

2. A compound in accordance with claim 1 wherein $CO_2M$ represents a carboxylate anion.

3. A compound in accordance with claim 1 wherein one R represents a group which contains a positively charged moiety, and the remaining R groups are selected from hydrogen and $C_{1-6}$ straight or branched chain alkyl, unsubstituted or substituted with one to four $R^d$ groups.

4. A compound in accordance with claim 3 wherein one R represents a group containing a positively charged moiety and the remaining R groups are hydrogen.

5. A method of treating or preventing a bacterial infection in a mammalian patient in need thereof, comprising administering to said patient an effective amount of a compound of claim 1.

6. A compound in accordance with claim 1 wherein the R group contain one positive charge balance by a carboxylate anion.

7. A compound in accordance with claim 1 wherein one R group represents a —$C_{1-6}$ straight or branched chain alkyl group, substituted with one to four $R^d$ groups, wherein one $R^d$ group represents —R* or Q.

8. A compound in accordance with claim 1 wherein Q is selected from the group consisting of:

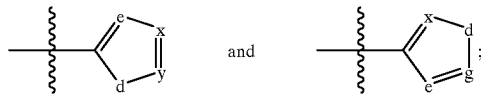

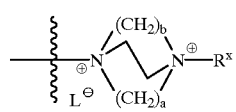

9. A compound in accordance with claim 8 wherein Q represents:

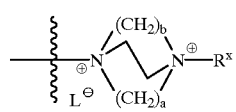

$L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups, and $R^h$, $R^i$ and $R^w$ are as originally defined.

10. A compound in accordance with claim 1 wherein Q represents —$N^+R^xR^yR^z$, wherein $R^x$, $R^y$ and $R^z$ are as originally defined.

11. A compound in accordance with claim 1 wherein one R* group is present and is selected from:

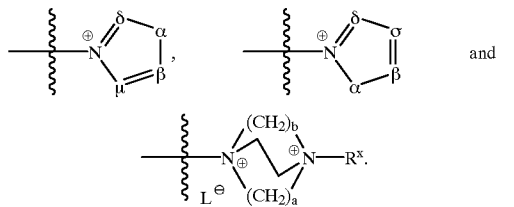

d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

12. A compound in accordance with claim 1 wherein:

$CO_2M$ represents a carboxylate anion;

one R group contains at least one positively charged moiety, and the remaining R groups are selected from hydrogen and $C_{1-6}$ straight or branched chain alkyl, unsubstituted or substituted with one to four $R^d$ groups;

$R^d$ is as originally defined;

$R^h$ represents hydrogen or a $C_{1-6}$ straight or branched chain alkyl group;

Q is selected from the group consisting of:

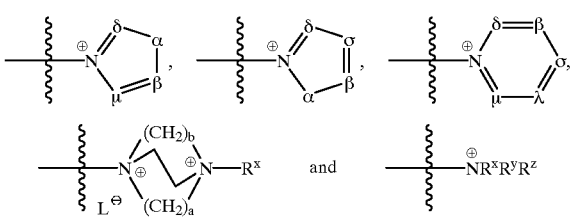

wherein $L^-$ is as originally defined; a and b represent 2, and $R^x$ represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NRhR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

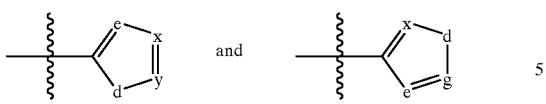

wherein d represents $NR^k$; $R^k$ represents $—C_{1-6}$ straight or branched chain alkyl; and e, g, x and y represent $CR^m$ or $N^+R^k$, with $R^k$ as defined above and $R^m$ representing hydrogen.

13. A compound in accordance with claim 1 wherein R is $A—(CH_2)_n—Q$, wherein A is O, S or $CH_2$ and n is 0—3 and Q is as originally defined.

14. A compound in accordance with claim 1 wherein Z is trans-CH=CH.

15. A compound in accordance with claim 1 wherein Z is C≡C.

16. A compound in accordance with claim 1 wherein X is iodine.

17. A compound in accordance with claim 1 represented by formula Ia:

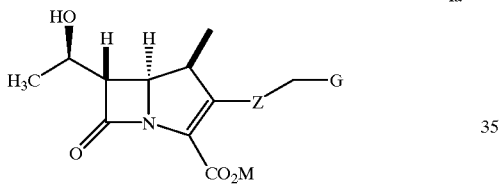

Ia wherein G is:

1
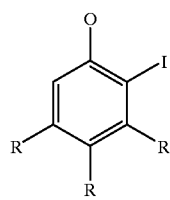

2
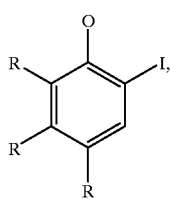

3
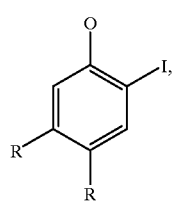

4
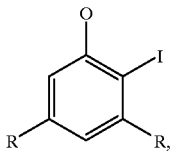

5
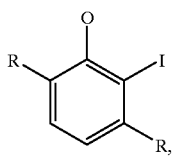

6
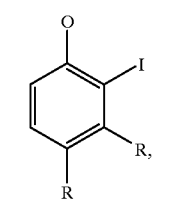

7
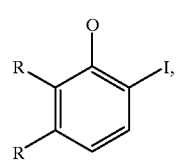

8
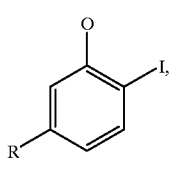

9
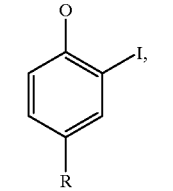

10
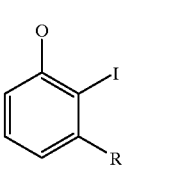 or

11 wherein:
Z is as originally described;
$CO_2M$ represents a carboxylate anion;
R group contains a positively charged moiety;
Rd is as originally defined;
$R^h$ represents hydrogen or a $C_{1-6}$ straight or branched chain alkyl group;

Q is selected from the group consisting of:

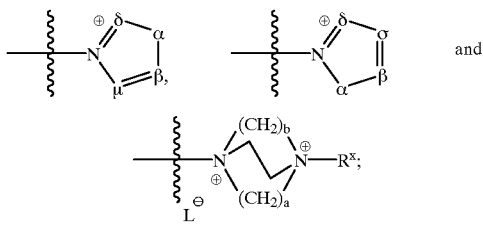

wherein L⁻, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl or heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

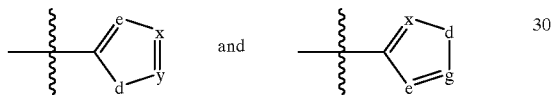

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

18. A compound in accordance with claim 17 wherein G is 1, 3–4, 6, 8, 9 or 10, R contains a positively charged moiety selected from the group consisting of: —R*, Q, A—$(CH_2)_n$—Q, and a $C_{1-6}$ straight or branched alkyl chain substituted with one $R^d$ group, wherein A is O, S, $CH_2$ and n is 0–3;

$R^d$ is independently —R* or Q;

Q is selected from the group consisting of:

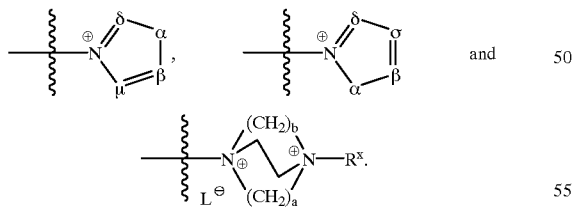

wherein L⁻, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NRhR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

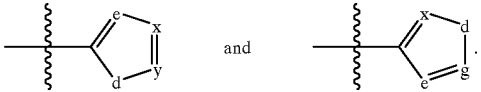

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

19. A compound according to claim 18 wherein G is 8 or 9.

20. A compound according to claim 1 represented by formula Ib:

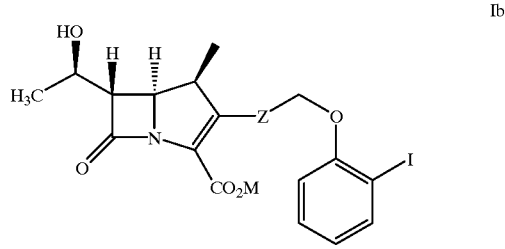

Ib or a pharmaceutically acceptable salt thereof, wherein:
Z is as originally described and $CO_2M$ represents a carboxylic acid or a pharmaceutically aceptable ester group.

21. A compound in accordance with claim 1 represented by formula Ic:

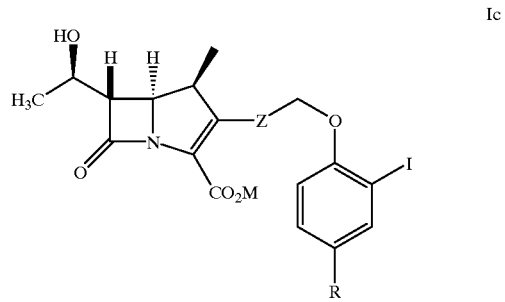

Ic wherein:
$CO_2M$ represents a carboxylate anion,
R represents

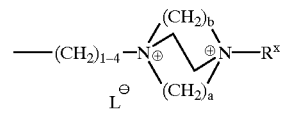

and $R^x$, a, b and L⁻ are as originally defined.

22. A compound in accordance with claim 1 wherein R represents A—$(CH_2)_n$—Q, wherein A is O, S or $CH_2$, n is 0–3 and Q is selected from the group consisting of:

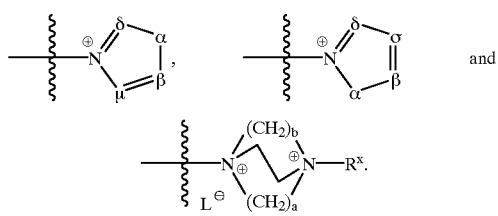 and

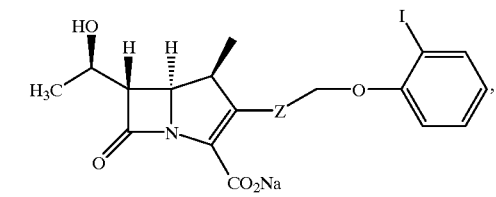

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups.

23. A compound which is:

E-1

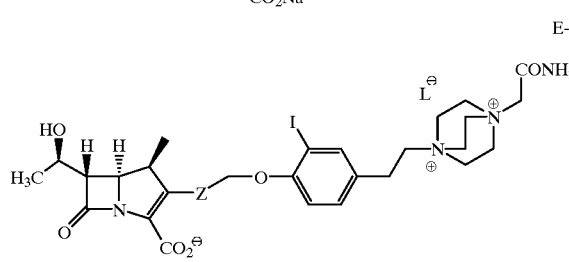

E-2

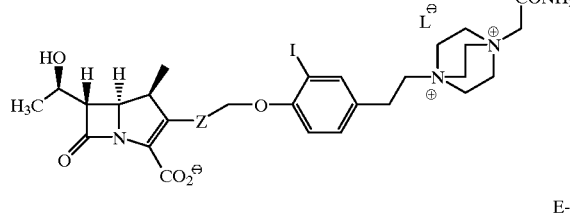

E-3

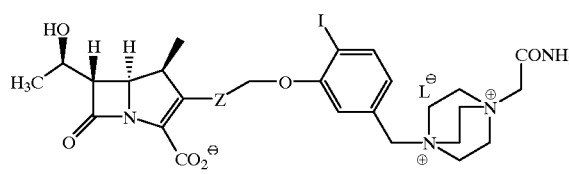

E-4

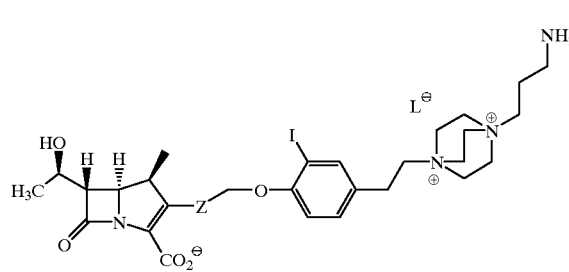

-continued

E-5

E-6

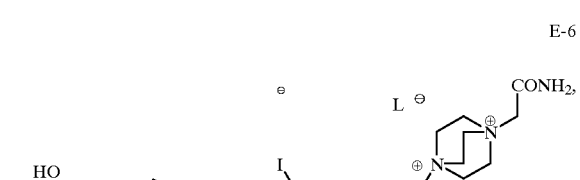

E-7

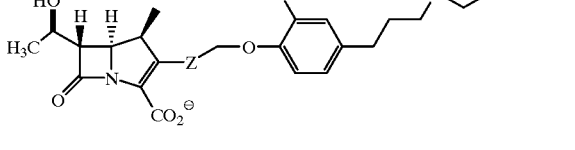

E-8

-continued
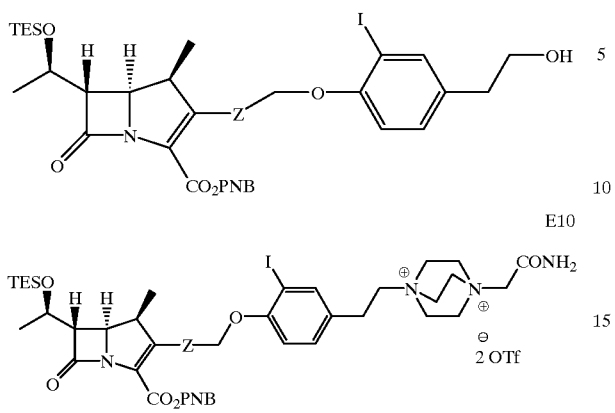
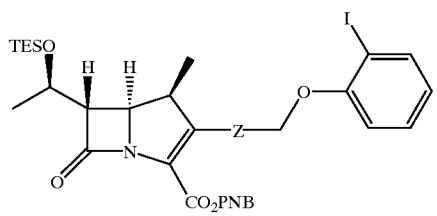
or the pharmaceutically acceptable salts thereof wherein PNB is p-nitrobenzyl. OTf is triflates, TES is triethylsilyl, and L⁻ is a pharmaceutically acceptable counterion.
24. A pharmaceutical composition comprised of a compound in accordance with claim 1 in combination with a pharmaceutically acceptable carrier.
* * * * *